United States Patent
Wieczorek et al.

(10) Patent No.: US 9,014,780 B2
(45) Date of Patent: Apr. 21, 2015

(54) IMAGE-BASED BIOPSY GUIDANCE METHOD

(75) Inventors: Herfried Wieczorek, Aachen (DE); Matthias Bertram, Aachen (DE)

(73) Assignee: Koninklijke Philips N.V., Eindhoven (NL)

(*) Notice: Subject to any disclaimer, the term of this patent is extended or adjusted under 35 U.S.C. 154(b) by 943 days.

(21) Appl. No.: 12/942,269

(22) Filed: Nov. 9, 2010

(65) Prior Publication Data

US 2011/0125011 A1    May 26, 2011

Related U.S. Application Data

(60) Provisional application No. 61/263,070, filed on Nov. 20, 2009.

(51) Int. Cl.
| | | |
|---|---|---|
| A61B 5/05 | (2006.01) | |
| A61B 6/03 | (2006.01) | |
| A61B 6/00 | (2006.01) | |
| A61B 19/00 | (2006.01) | |
| A61B 10/02 | (2006.01) | |
| G01R 33/48 | (2006.01) | |

(52) U.S. Cl.
CPC ............... *A61B 6/032* (2013.01); *A61B 6/037* (2013.01); *A61B 6/4233* (2013.01); *A61B 6/487* (2013.01); *A61B 6/5235* (2013.01); *A61B 6/5264* (2013.01); *A61B 10/0233* (2013.01); *A61B 19/50* (2013.01); *A61B 2019/507* (2013.01); *A61B 2019/5265* (2013.01); *A61B 2019/5289* (2013.01); *G01R 33/481* (2013.01); *A61B 6/4417* (2013.01)

(58) Field of Classification Search
USPC .................................. 600/407, 425, 427, 436
See application file for complete search history.

(56) References Cited

U.S. PATENT DOCUMENTS

| | | | |
|---|---|---|---|
| 6,575,969 B1* | 6/2003 | Rittman et al. | 606/41 |
| 6,878,941 B2* | 4/2005 | Balan et al. | 250/363.02 |
| 7,378,660 B2* | 5/2008 | Case et al. | 250/363.01 |
| 7,394,053 B2 | 7/2008 | Frangioni et al. | |
| 2006/0002630 A1* | 1/2006 | Fu et al. | 382/294 |
| 2007/0055129 A1 | 3/2007 | Graumann | |
| 2008/0275467 A1 | 11/2008 | Liao et al. | |
| 2011/0026786 A1* | 2/2011 | Mohamed | 382/128 |

OTHER PUBLICATIONS

Vermeeren et al., "Intraoperative Radioguidance With a Portable Gamma Camera: a novel trechnique for laparoscopic sentinel node localisation in urological malignancies", Mar. 14, 2009, European Journal of Nuclear Medicine and Molecular Imaging, vol. 36, pp. 1029-1036.*

Siemens (herein the Brochure), "Symbia TruePoint SPECT-CT", 2005, pp. 1-20.*

Olmos, R.A.V.,et al.; SPECT-CT and real-time intraoperative imaging: new tools for sentinel node localization and radioguided surgery?; 2009; Eur. J. Nucl. Med. Mol. Imaging: 36: pp. 1-5.

Van Der Ploeg, I.M.C., et al.; The hidden sentinel node and SPECT/CT in breast cancer patients; 2009; Eur J Nucl Med Mol Imaging; 36:pp. 6-11.

* cited by examiner

*Primary Examiner* — James Kish

(57) ABSTRACT

When performing image-guided biopsy of an anatomical structure in a patient, a target anatomical patient region containing biopsy target is imaged using both SPECT and XCT concurrently. 3D SPECT and XCT image data is fused to generate a fused 3D reference image that is overlaid on 2D patient image(s) generated during the biopsy procedure to generate an overlay image. The overlay image also includes a planned path or trajectory for a biopsy instrument. The 2D patient images are generated using SPECT and/or XCT, and are updated periodically to show biopsy instrument position and progress.

22 Claims, 3 Drawing Sheets

IMAGE-BASED BIOPSY GUIDANCE METHOD

CROSS REFERENCE TO RELATED APPLICATIONS

This application claims the benefit of U.S. provisional application Ser. No. 61/263,070 filed Nov. 20, 2009, which is incorporated herein by reference.

DESCRIPTION

The present application finds particular utility in minimally invasive medical procedures and systems. However, it will be appreciated that the described technique(s) may also find application in other types of medical systems, other biopsy systems, and/or other medical applications.

Breast cancer is the number one killer in women under the age of 60. Since breast cancer has a simple superficial drainage pattern, for treatment of breast carcinoma it is highly relevant to find out whether sentinel lymph nodes are affected or not. Classical procedures with biopsy-proven carcinoma involve axillary dissection and have significant side effects and morbidity, and 60% of patients are found free from metastases, which makes this method questionable.

Conventionally, minimally invasive instruments, such as biopsy needles, are tracked using a C arm x-ray system in a fluoroscopic mode. On some occasions, the C arm x-ray unit is supplemented with a single detector nuclear camera such that a planar x-ray and a planar SPECT image are generated. In some instances, the planar fluoroscopy image is combined with a previously generated three dimensional CT image.

Another standard procedure is Sentinel Lymph Node Biopsy (SLNB). After identification of the sentinel nodes by lymph node mapping, excision and biopsy of the nodes are done before deciding on further treatment. This method has a high negative predictive value and at the same time avoids the complications of unnecessary dissection. Lymph node mapping may be based on palpation, ultrasound, planar lymphoscintigraphy, and coloring by blue dyes. However, this approach falls short when certain circumstances are present, including non-palpable nodes, non-visualization, an unknown number of sentinel nodes (up to three sentinel nodes; more than one in 20% of patients), and in particular the presence of deep-lying and non-axillary nodes. Due to missing anatomical information in planar scintigraphy, only 85% of sentinel nodes are found using this approach, even by experienced surgeons.

The use of combined single photon emission computed tomography (SPECT)/computed tomography (CT) instead of planar scintigraphy is promoted in the literature (Eur. J. Nucl. Med. Mol. Imaging 36, pp. 1-5 and 6-11, 2009). One advantage of this method is primarily seen in breast cancer and melanoma, and further in gastrointestinal, gynecological, and urological malignancies where sentinel nodes are found in deep locations. The present inventors have determined that the BrightView™ gantry equipped with x-ray computed tomography (XCT) (by Philips) is well suited for sentinel lymph node mapping due to the excellent spatial resolution of the XCT system. However, traditional SPECT/XCT systems have not been adapted for biopsies.

There is an unmet need in the art for systems and methods that facilitate using combined SPECT/CT imaging systems for sentinel lymph node biopsies, and the like, thereby overcoming the deficiencies noted above.

In accordance with one aspect, a system that facilitates image-guided biopsy includes a multi-modal imaging device comprising at least two imaging modalities, which generates images of an anatomical region of a patient including a target region, and a processor that executes computer-executable instructions stored in a memory. The instructions comprise mapping a biopsy target in the target region using at least one of the imaging modalities. The instructions further comprise monitoring a position of a biopsy instrument in the patient during a biopsy procedure by imaging the target region using one of the at least two imaging modes provided by the multi-modal imaging device in order to generate at least two real-time 2D images that are angularly offset from each other. The instructions further comprise generating 2D overlay images by projecting a planned biopsy instrument trajectory from the fused 3D reference image into the real-time 2D images of the target region.

In accordance with another aspect, a method of performing image-guided biopsy of a biopsy target in a target region of a patient includes planning a trajectory for a biopsy instrument from an entry point to a target in the target region. The method further includes monitoring current positions of the biopsy instrument in the target region during a biopsy procedure by imaging the target region using one of the at least two imaging modalities of the multi-modal imaging device in order to generate a series of real-time 2D images, and generating overlay 2D images by projecting the planned trajectory from the fused 3D reference image into the real-time 2D image of the target region during the biopsy procedure.

In accordance with another aspect, a method of performing image-guided sentinel lymph node (SLN) biopsy includes mapping one or more sentinel lymph nodes in a target region using single photon emission computed tomography (SPECT) and x-ray computed-tomography (XCT). The method further includes monitoring a position of a biopsy instrument in the patient during a biopsy procedure by imaging the target region using one of SPECT cameras positioned at a fixed 90° orientation relative to each other about an examination region in which the target region is positioned, and an x-ray source and a flat-panel x-ray detector. The method further includes generating overlay images by projecting a planned biopsy instrument path from the fused 3D reference image into a real-time 2D image of the target region generated during the biopsy procedure, and monitoring and compensating for patient movement during the biopsy procedure.

According to another aspect, a method of performing a multi-modal image-guided interventional procedure on a patient comprises mapping a target volume in a target region of a patient by generating single photon emission computed tomography (SPECT) image data and x-ray computed-tomography (XCT) image data of the target region in a common imaging plane. The method further comprises monitoring a position of an instrument in the patient during an interventional procedure by imaging the target region using one of retractable SPECT cameras, and an x-ray source and retractable flat-panel x-ray detector. The method further comprises generating overlay images by projecting a planned instrument path from a fused 3D reference image into a real-time 2D image of the target region generated during the interventional procedure, and monitoring and compensating for patient movement during the biopsy procedure. The flat-panel x-ray detector is retracted to a stowed position during SPECT imaging, and the SPECT cameras are retracted into a stowed position during XCT imaging.

One advantage is that biopsy plan quality is improved.

Another advantage resides in improving image quality for biopsy procedures.

Still further advantages of the subject innovation will be appreciated by those of ordinary skill in the art upon reading and understand the following detailed description.

The drawings are only for purposes of illustrating various aspects and are not to be construed as limiting.

Figure 1:
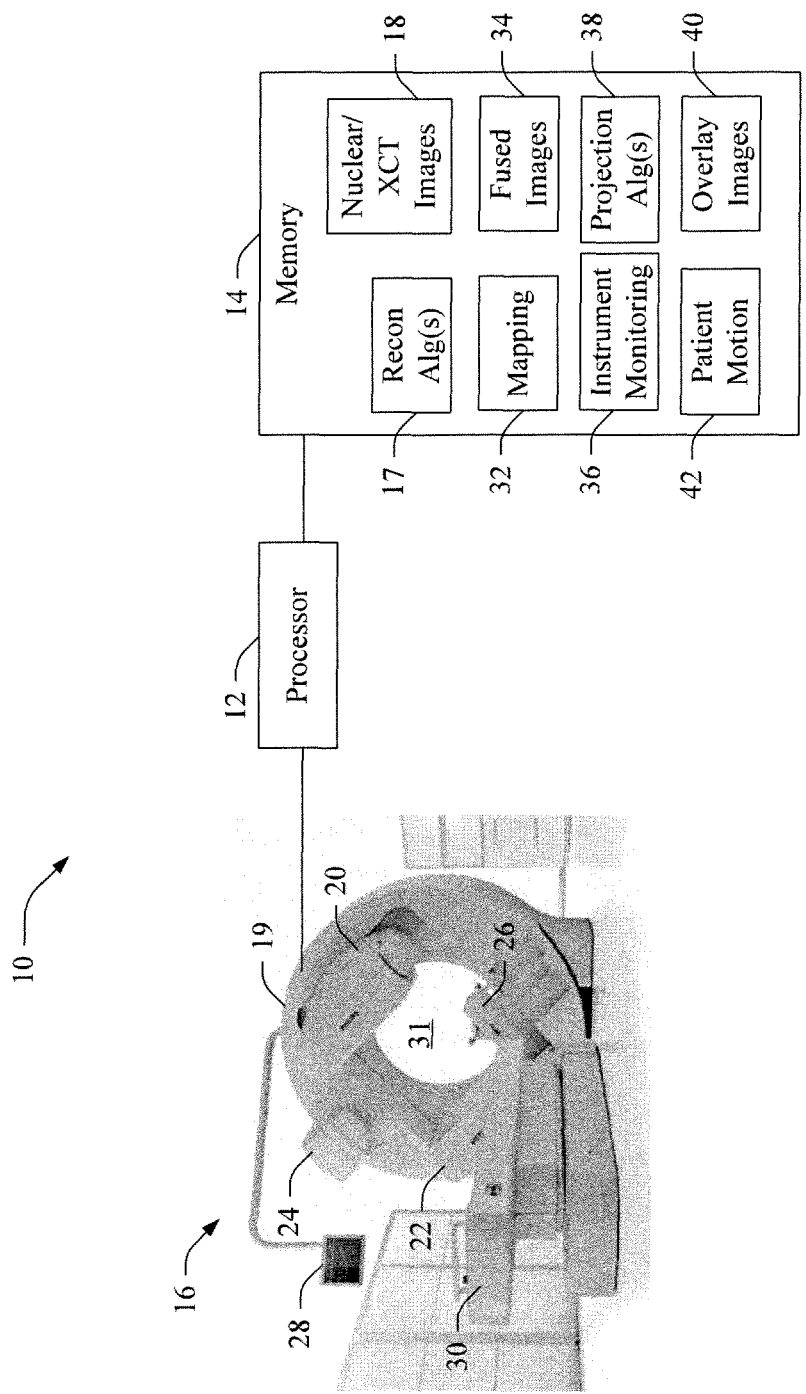
FIG. 1 illustrates a system that facilitates using combined SPECT/XCT image data to guide a biopsy procedure in a patient, in accordance with one or more aspects described herein.

Patient anatomy mapping and biopsy are increasingly important methods in oncology. For example, sentinel lymph node (SLN) biopsy is a new standard procedure that avoids axillary dissection (AD) its side effects, among them significant morbidity, and is especially useful in the breast cancer care cycle. SLN biopsies may be performed under x-ray, CT or nuclear camera guidance. Since Philips' BrightView™ system with its high XCT spatial resolution is very well suited to lymph node mapping, biopsies may be guided on the same system, in accordance with various embodiments described herein. For example, the flat-panel design of the XCT system provides good spatial resolution, while the small footprint of the system allows it to be used in interventional applications that cannot accommodate larger, traditional multi-modal imaging systems. Additionally, the multi-modal XCT system employs a common imaging plane for multiple imaging modes, which facilitates fusing image data from the multiple modes. The geometry of the detector heads permits an operator to move (e.g., retract to a stowed position) one or more heads out of the way during XCT imaging or when an interventionist needs to access the patient, and/or to fold the flat-panel x-ray detector into a stowed position during nuclear imaging. One or more of the nuclear cameras and the x-ray detector may also be moved to a stowed position to permit a clinician or interventionist to access the patient, such as during a biopsy procedure or the like. Moreover, the relatively slow rotation (e.g., approximately 5 rpm or less) of the imaging components (e.g., detectors, cameras, sources, etc.) improves safety for the patient and the operator.

For instance, a method to perform the biopsy under x-ray and/or nuclear camera guidance utilizes 3D fused images from the BrightView/XCT system. In one embodiment, the target location and the planned needle path from the 3D images are overlaid onto real-time X-ray or nuclear camera projections, enabling clear progress monitoring during the biopsy. In case of patient movement between acquisition of the 3D data and the biopsy, the 3D images are updated and/or shifted according to information extracted from the real-time image data. In this manner, the systems and methods described herein facilitate performing biopsies on the XCT system. The methods may easily be adapted to other applications, such as bone biopsies.

It will be appreciated that the described systems and methods employ dual imaging modalities, wherein combined SPECT/XCT imaging modalities are described by way of example, although other combinations are contemplated. For instance, the described systems and methods may employ combined positron emission tomography (PET)/computed tomography (CT), SPECT/magnetic resonance imaging (MRI), PET/MRI, SPECT/ultrasound, PET/ultrasound, or any other suitable multi-modal imaging technique. The multi-modality of the herein-described systems provides several advantages, such as facilitating generation of functional images while permitting the use of targeted molecular agents (e.g., tracers, markers, etc.) and the like. Additionally, although many examples described herein relate to SNL mapping and biopsy, it will be appreciated that the described systems and methods may be employed to guide biopsy of any suitable anatomical structure, as well as for other medical procedures.

FIG. 1 illustrates a system 10 that facilitates using combined SPECT/XCT image data to guide a biopsy procedure in a patient, in accordance with one or more aspects described herein. The system includes at least one processor 12 coupled to a memory 14 and to a SPECT/XCT imaging device 16. The processor executes one or more reconstruction algorithms 17 to reconstruct raw SPECT and/or XCT data to generate respective SPECT and/or XCT images 18. Taken together, the processor and the reconstruction algorithms define a means for reconstructing SPECT and/or x-ray projection images. Other means, such as one or more dedicated reconstruction processors and the like are also contemplated. The imaging device 16 includes a rotatable gantry 19, on which are mounted a first nuclear camera 20 and a second nuclear camera 22. The gantry may be rotated at a relatively slow speed (e.g., 5 rpm or less) during image data acquisition to reduce risk of injury to patients and/or operators. Also mounted to the gantry are a CT (e.g., XCT) source 24, e.g. an x-ray tube or other means for generating x-rays, and a flat-panel x-ray detector 26. The nuclear cameras and x-ray detector are retractable and stowable such that the nuclear cameras can be stowed out of the way during XCT imaging, and the x-ray detector can be folded into a stowed position during nuclear imaging. A display 28 is mounted on the imaging device and presents one or more image representations to a user. A patient couch or table 30 is provided that supports a patient during translation of the patient into and out of an examination region 31 during SPECT/XCT data acquisition.

As mentioned above, the system includes the processor 12 that executes, and the memory 14 that stores, computer executable instructions for carrying out the various functions and/or methods described herein. The memory 14 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 12 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The memory 14 stores a biopsy target mapping algorithms 32 (i.e., a set of computer-executable instructions) that is executed by the processor to map a biopsy target (e.g., sentinel lymph nodes or some other target) in the patient. Taken together, the mapping algorithms and the processor define a means for mapping positions of one or more biopsy targets in a target region of a patient. Fused images 34 comprising SPECT and XCT image data are generated by the processor and stored in the memory. That is, when biopsy target mapping is performed on the BrightView™ system, a two-fold 3D data set is generated that shows the exact anatomical location of the biopsy target(s) and is the basis for planning of the exploration route for the biopsy procedure. Particularly, the XCT image defines the patient anatomy in 3D and the SPECT or other functional image defines the locations in the 3D XCT image that selectively absorb a radio-active tracer, e.g., the sentinel nodes. According to another embodiment, only one of the imaging modalities is employed to map the biopsy target.

Once the biopsy procedure has begun, the processor executes an instrument monitoring algorithm 36 to track the position of an instrument (e.g., a needle, tweezers, or other biopsy instrument) in the patient. Instrument monitoring can be performed using the XCT source and detector, the nuclear cameras, or a combination thereof. Taken together the instrument tracking algorithm and the processor define means for tracking and/or monitoring biopsy instrument position within the patient.

To provide further guidance during the actual biopsy, the combined 3D images are used as a roadmap by overlaying them with real-time planar X-ray images (e.g., generated from ACT acquisition data) and/or real-time scintigrams (e.g., generated from nuclear camera acquisition data). The processor 12 executes a projection algorithm 38 that overlays the 3D SPECT/XCT data onto the 2D planar X-ray and/or scintigram image data. Overlay images 40 generated in this manner are stored to the memory 14 and presented to the user on the display 28. Taken together the processor and projection algorithm provide means for projecting or overlaying 3D SPECT/XCT data onto 2D planar image data and/or scintigram data. Additionally, the processor executes a patient motion algorithm 42 to account for patient motion between the biopsy and the mapping stages, and/or patient movement during the biopsy procedure. Taken together, the processor and patient motion algorithm provide means for monitoring and compensating for patient motion prior to and/or during biopsy procedure.

According to one embodiment, Philips' BrightView™ SPECT/XCT camera is used for SLN biopsy following SLN mapping on the same device. Fused preoperative SPECT and XCT images 34 are used as a reference image for the biopsy. During biopsy, the position of the needle, laparoscopic tweezers or any other equipment used, is monitored either with the flat x-ray detector 26 under fluoroscopic low dose conditions in a plane that may be changed during operation and/or by the nuclear camera images of one or both BrightView detectors 20, 22, e.g., taken under 90° fixed angle. A detailed roadmap and progress-monitoring of the biopsy is achieved by projecting the target region and the planned needle path from the 3D fused images 34 into the real-time X-ray and/or nuclear camera images to generate the overlay images 40.

The biopsy needle and/or other equipment can be marked by radioactive seeds when identification by the nuclear cameras is intended (which may include the use of different isotopes for lymph nodes labeling and marking of equipment, see for example R. A. Valdes Olmos et al, EJNMMI 36, pp. 1-5 (2009)). Any patient movement is monitored in a manner similar to that used for detection of the needle position so that an updated XCT and SPECT volume image of the patient is available during biopsy.

With regard to the system of FIG. 1, and the methods described below with regard to FIGS. 2 and 3, fused XCT and SPECT 3D data are used as a reference during operation. In a planning stage, a planned trajectory or path is optionally drawn on the fused 3D image denoting a path from an entry point to the target. For guidance, the fused 3D data, which may be previously recorded, is overlaid with the real-time images data taken during the biopsy. In one embodiment, only one 3D imaging modality is used to map the biopsy target. In another embodiment, when using real-time guidance with the X-ray detector or the nuclear cameras, the overlay is done such that the planned needle path and the position of the target region are projected into these planar projections according to the current projection directions. By projecting the inserted instrument and the planned trajectory onto two orthogonal planar images a clear progress of the needle or other instrument to the target is monitored and any deviation from the planned trajectory can be corrected. In another embodiment, a 2D view plane perpendicular to the planned trajectory can minimize foreshortening effects in the progress view.

In an embodiment in which real-time guidance by the nuclear cameras is used during operation, the two nuclear cameras are positioned at a 90° offset, preferentially in an over head or under table position of one camera and a side position of the other camera, or any other position where the two cameras are at a fixed angle of 90° and provide maximum possible accessibility for the physician. This stereoscopic view facilitates showing the exact position of point-like sources like lymph nodes or radioactively marked laparoscopic tweezers or other instruments in the fused 3D images. Should the patient have moved between acquisition of the 3D data sets and the biopsy procedure, the patient position is intermittently updated by planar x-ray images under low dose conditions and under two or more imaging angles to get 3D information. In case the positioning of the patient is strongly different from the pre-operative position, an updated 3D XCT image of the relevant part of the patient is acquired. As an alternative to the update of the patient position by x-ray, the update the 3D images for motion correction is performed based on the updated position of relevant lymph nodes or other landmarks seen in the two orthogonal nuclear camera images. For example, a transform between the planning 3D XCT image and the current 3D XCT image is applied to the fused 3D image to transform it to the current location.

Laparoscopic needles, tweezers, or other instruments may be marked by other isotopes than isotopes used for labeling lymph nodes (often nanocolloids including Tc-99m), e.g. I-125, I-123, Am-241, or others in order to differentiate between lymph node and laparoscopic equipment in the nuclear camera image. On the BrightView™ system, this method is employed to directly visualize node and needle position in the 3D data of the pre-operative fused SPECT/XCT image(s) 34.

Figure 2:
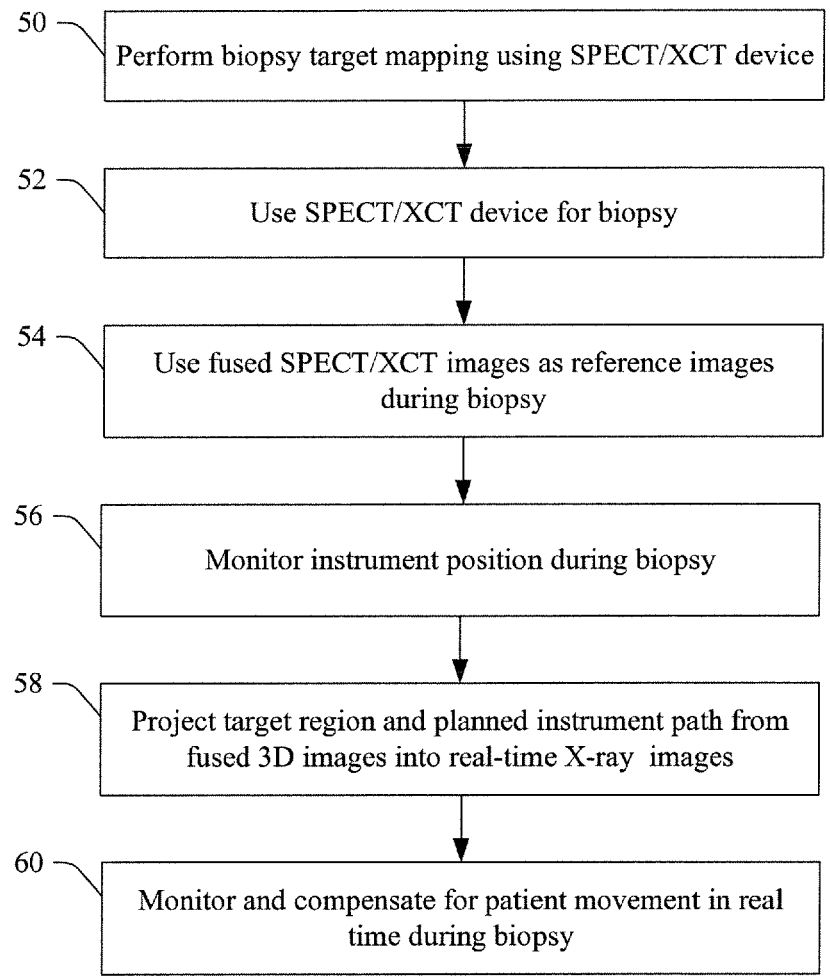
FIG. 2 illustrates a method for SPECT/XCT image guided biopsy using real-time X-ray images, in accordance with various aspects described herein.

FIG. 2 illustrates a method for SPECT/XCT image guided biopsy using real-time X-ray images, in accordance with various aspects described herein. At 50, biopsy target mapping is performed using the combined SPECT/XCT imaging device 16 to generate the fused SPECT/XCT 3D image. In one embodiment, the biopsy target is a sentinel lymph node. At 52, the SPECT XCT imaging device is employed again during a biopsy or other procedure. At 54, the fused SPECT/XCT 3D images are employed as reference images during the biopsy procedure. At 56, the instrument position is monitored by generating x-ray images, preferably pairs of orthogonal x-ray images, as the gantry 19 rotates. The instrument may be a needle, tweezers, or other suitable biopsy instrument. At 58, the target region within the patient and a planned instrument trajectory are projected from the fused 3D images into real-time 2D X-ray images of the patient. For example, a single x-ray source and detector can rotate around the patient. One of the 2D XCT images can be updated every 90° of rotation.

Because the instrument is typically inserted slowly, an update every few seconds is typically adequate. At 60, patient motion is monitored, and the fused 3D images or the projections of the fused 3D images are adjusted in real time to compensate for any monitored patient motion.

The biopsy target mapping at 52 can be performed at any time prior to performing the biopsy. An XCT scan is performed during the biopsy to determine patient position, and adjustment is made for any inconsistency between the patient position during mapping and the patient position during XCT scan during the biopsy procedure. The planned needle path and target region generated using the fused SPECT/XCT 3D image data from the mapping stage is then overlaid or projected onto the 2D XCT patient image taken during the biopsy procedure. The XCT images are updated periodically during the biopsy to account for patient motion during the procedure, and the overlaid 3D image is adjusted accordingly.

Figure 3:
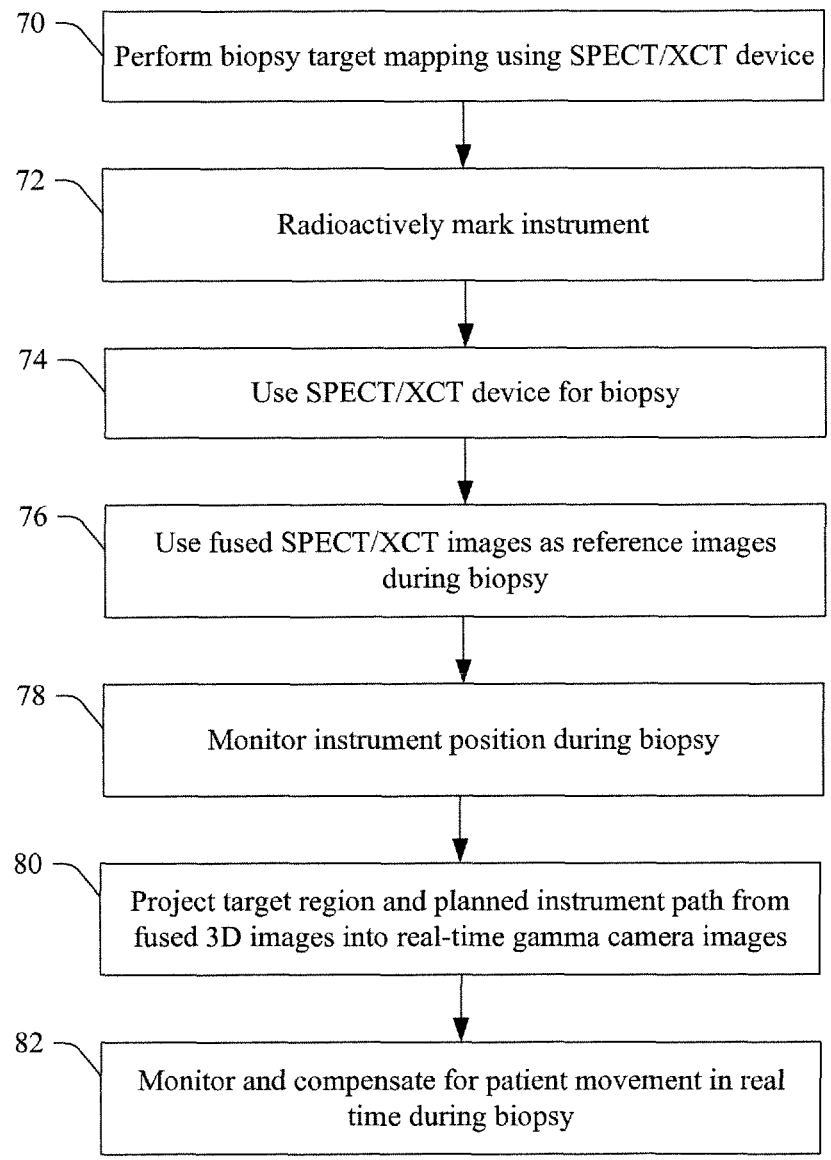
FIG. 3 illustrates a method for SPECT/XCT image guided biopsy using real-time nuclear camera images, in accordance with various aspects described herein.

FIG. 3 illustrates a method for SPECT/XCT image guided biopsy using real-time nuclear camera images, in accordance with various aspects described herein. At 70, biopsy target mapping is performed on a patient using the SPECT/XCT imaging device 16 to generate the 3D SPECT/XCT image. At 72, a biopsy instrument (e.g., a needle, probe, tweezers, etc.) is marked with radioactive material, to make it visible or detectable by one or more nuclear cameras 20, 22. It will be appreciated that marking the biopsy instrument can be performed at any time prior to performing the biopsy procedure, e.g. or the time of manufacture, immediately preceding the procedure or the like. At 74 the SPECT/XCT imaging device is employed for real-time image-guided biopsy. At 76, the fused SPECT/XCT image is used as one or more reference images during the biopsy procedure. A current, real time position and location of the instrument is monitored in real-time during the biopsy procedure, at 78. In one embodiment, the two nuclear cameras are mounted 90° to each other and sampled periodically. In another embodiment, the nuclear cameras are mounted opposite each other and the gantry rotates in 90° increments in a step-and-shoot mode. Both embodiments generate sets of orthogonal 2D projection images. At 80, a target region (e.g., an anatomical region of the patient containing the biopsy target) and a planned instrument trajectory from the surface of the patient to the biopsy target are projected from the fused SPECT/XCT 3D reference image into the 2D real-time nuclear camera images of the target region. At 82, patient movement is monitored and compensated for in real-time during the biopsy. For example, the x-ray source 26 and the x-ray detector 24 rotate around the patient and generate images periodically which are compared with corresponding projections of the 3D reference image or reconstructed into a 3D image which is compared with the 3D reference image to determine changes in patient position, i.e. motion.

The described systems and methods thus facilitate generating a 3D SPECT image and a 3D XCT image using, e.g., a Philips BrightView™ scanner. In one embodiment, nuclear and x-ray 3D images are combined or fused to highlight tumors and concurrently provide an anatomical road map for inserting a biopsy instrument into the patient to a biopsy target. The minimally invasive procedure is planned using the fused 3D reference image. To track the minimally invasive instrument, the fused 3D image is used in conjunction with a pair of orthogonal projection x-ray images, a pair of orthogonal SPECT images, or a pair of orthogonal combined SPECT/x-ray images. In order to track the minimally invasive instrument using a SPECT camera, a fluoroscopic substance is attached to or incorporated in the instrument. An additional XCT image can be generated before starting the minimally invasive procedure to confirm the alignment between the patient and the fused 3D image. Additional fused or XCT images can be generated, as needed, to be sure that the alignment is maintained.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates image-guided biopsy, including:
    a multi-modal imaging device comprising at least two imaging modalities, which generates images of an anatomical region of a patient including a target region;
    a processor that executes computer-executable instructions stored in a memory, the instructions comprising:
        mapping a biopsy target in the target region by generating images of the biopsy target using at least one of the imaging modalities;
        monitoring a position of a biopsy instrument in the patient during a biopsy procedure by imaging the target region using one of the at least two imaging modalities provided by the multi-modal imaging device and generating at least two real-time planar 2D images that are orthogonal to each other;
        generating 2D overlay images by projecting a planned biopsy instrument trajectory and biopsy instrument position into the at least two orthogonal planar real-time 2D images of the target region;
        generating, from the at least two 2D overlay images, a fused 3D reference image of the target region and the planned biopsy instrument trajectory;
        monitoring and compensating for patient movement by updating patient position in the 2D overlay images and the fused 3D reference image during the biopsy procedure, wherein updating patient position is performed by rotating an x-ray source and a flat panel x-ray detector on a gantry and generating image data that is compared with the fused 3D reference image to determine patient movement;
        wherein monitoring the position of the biopsy instrument further comprises periodically generating and displaying updated 2D overlay images of the target region that show biopsy instrument position and progress relative to the target region and the biopsy target; and
        wherein the x-ray source and x-ray detector are positioned in a 90° orientation relative to the biopsy path thereby mitigating foreshortening effects in x-ray image data.

2. The system according to claim 1, further comprising:
    mapping the biopsy target using at least two of the imaging modalities; and
    generating the fused 3D reference image of the target region and planned trajectory by fusing 3D image data acquired, while mapping the biopsy target, in a common imaging plane by the at least two imaging modalities;
    wherein the fused 3D reference image includes 3D nuclear image data combined with 3D x-ray computed tomography (XCT) image data.

3. The system according to claim 1, wherein the multi-modal imaging device includes at least two nuclear cameras, an x-ray source, and a flat-panel x-ray detector.

4. The system according to claim 3, wherein the nuclear cameras include single photon emission computed tomography (SPECT) cameras.

5. The system according to claim 3, wherein the instructions further include:
prior to the biopsy procedure, retracting the nuclear cameras into a stowed position;
monitoring the position of the biopsy instrument in the patient during the biopsy procedure by imaging the target region using the x-ray source and flat panel x-ray detector; and
periodically generating updated 2-D x-ray images of the target region that show biopsy instrument position and progress relative to the trajectory and the biopsy target.

6. The system according to claim 3, wherein the instructions further include:
monitoring the position of the biopsy instrument in the patient during the biopsy procedure by imaging the target region using the at least two nuclear cameras; and
periodically generating updated nuclear images of the target region that show biopsy instrument position and progress relative to the target region and the biopsy target.

7. The system according claim 6, wherein the biopsy instrument comprises a radioactive marker applied prior to performing the biopsy procedure, wherein the radioactive marker is detectable by the nuclear cameras.

8. The system according to claim 6, wherein the nuclear cameras have a fixed 90° orientation relative to each other during the biopsy procedure.

9. The system according to claim 6, wherein the nuclear cameras are mounted on a gantry that rotates the nuclear cameras to 90° offset positions around the patient.

10. A method of performing image-guided biopsy of a biopsy target in a target region of a patient, including:
generating images of a biopsy target in a target region;
planning a trajectory for a biopsy instrument from an entry point to the target in the target region;
monitoring current positions of the biopsy instrument in the target region during a biopsy procedure by imaging the target region using one of at least two imaging modalities of a multi-modal imaging device and generating a series of angularly-offset planar real-time 2D images;
generating overlay 2D images by projecting the planned trajectory and biopsy instrument position into at least two angularly offset planar real-time 2D images of the target region during the biopsy procedure;
generating, from the at least two angularly offset planar real-time 2D images, a fused 3D reference image of the target region and the planned biopsy instrument trajectory;
monitoring and compensating for patient movement in the at least two angularly offset planar real-time 2D images and the a fused 3D reference image by updating patient position during the biopsy procedure, wherein updating patient position is performed by rotating an x-ray source and a flat panel x-ray detector on a gantry, and generating image data that is compared with the fused 3D reference image to determine patient movement;
wherein monitoring the position of the biopsy instrument further comprises periodically generating and displaying updated overlay 2D images of the target region that show biopsy instrument position and progress relative to the target region and the biopsy target; and
wherein the x-ray source and x-ray detector are positioned in a 90° orientation relative to the biopsy path thereby mitigating foreshortening effects in x-ray image data.

11. The method according to claim 10, wherein generating the fused 3D reference image includes:
rotating at least two nuclear cameras, an x-ray source, and a retractable flat-panel x-ray detector concurrently around the target region;
generating 3D nuclear image data and 3D x-ray computed tomography data in a common imaging plane with the nuclear cameras, the x-ray source, and the flat-panel x-ray detector; and
generating the fused 3D image by reconstructing the 3D nuclear image data and the 3D x-ray image data.

12. The method according to claim 11, wherein the nuclear cameras include single photon emission computed tomography (SPECT) cameras.

13. The method according to claim 11, further including rotating a gantry, to which the nuclear cameras, the x-ray source, and the flat-panel x-ray detector are mounted, at a speed of approximately 5 rpm or less during data acquisition.

14. The method according to claim 10, wherein monitoring the current position of the biopsy instrument includes:
during the biopsy procedure, retracting the nuclear cameras into a stowed position and imaging the target region using the x-ray source and flat-panel x-ray detector; and
periodically generating updated x-ray computed tomography (XCT) images of the target region that show biopsy instrument position and progress relative to the target region and the biopsy target.

15. The method according to claim 10, further comprising radioactively marking the biopsy instrument with at least one of Iodine-125, Iodine-123, and Americium 241 prior to performing the biopsy procedure to thereby make the biopsy instrument detectable by the nuclear cameras, and wherein monitoring the current position of the biopsy instrument during the biopsy procedure includes:
generating the real-time 2D images using the at least two nuclear cameras.

16. The method according to claim 15, further comprising:
positioning the nuclear cameras in a fixed 90° orientation relative to each other during the monitoring of the position of the biopsy instrument.

17. The method of claim 10, wherein the biopsy target is a sentinel lymph node.

18. A method of performing image-guided sentinel lymph node (SLN) biopsy, including:
mapping one or more sentinel lymph nodes in a target region by generating images thereof using single photon emission computed tomography (SPECT) and x-ray computed-tomography (XCT);
monitoring a position of a biopsy instrument in the patient during a biopsy procedure by imaging the target region using one of:
SPECT images generated by SPECT cameras positioned at a fixed 90° orientation relative to each other about an examination region in which the target region is positioned; and
x-ray images generated by an x-ray source and flat-panel x-ray detector;
generating overlay images by overlaying biopsy instrument position, and a planned biopsy instrument path from a fused 3D reference image, onto at least two orthogonal planar real-time 2D images of the target region generated during the biopsy procedure;
monitoring and compensating for patient movement by updating patient position in the orthogonal planar real-time 2D images and the fused 3D reference image during the biopsy procedure, wherein updating patient position is performed by rotating the x-ray source and the flat panel x-ray detector on a gantry and generating image data that is compared with the fused 3D reference image to identify patient movement;

wherein monitoring the position of the biopsy instrument further comprises periodically generating and displaying updated images of the target region that show biopsy instrument position and progress relative to the target region and the biopsy target; and wherein the x-ray source and x-ray detector are positioned in a 90° orientation relative to the biopsy path thereby mitigating foreshortening effects in x-ray image data.

19. The method according to claim 18, further comprising: generating the fused 3D reference image of the target region by fusing 3D SPECT image data and 3D XCT image data acquired while mapping the one or more sentinel lymph nodes.

20. The method according to claim 19, wherein the 3D SPECT image data and the 3D XCT image data are acquired in a common imaging plane.

21. A method of performing a multi-modal image-guided interventional procedure on a patient, comprising:
mapping a target volume in a target region of a patient by generating single photon emission computed tomography (SPECT) image data and x-ray computed-tomography (XCT) image data of the target region in a common imaging plane;
monitoring a position of an instrument in the patient during an interventional procedure by imaging the target region using one of:
SPECT images generated by retractable SPECT cameras; and
x-ray images generated by an x-ray source and retractable flat-panel x-ray detector;
generating overlay images by overlaying the position of the instrument, and a planned instrument path from a fused 3D reference image, onto at least two orthogonal planar real-time 2D images of the target region generated during the interventional procedure;
monitoring and compensating for patient movement by updating patient position in the orthogonal planar real-time 2D images and the fused 3D reference image during the biopsy procedure, wherein updating patient position is performed by rotating the x-ray source and the flat panel x-ray detector on a gantry thereby generating image data that is compared with the fused 3D reference image to determine patient movement;
wherein monitoring the position of the biopsy instrument further comprises periodically generating and displaying updated images of the target region that show biopsy instrument position and progress relative to the target region and the biopsy target;
wherein the x-ray source and x-ray detector are positioned in a 90° orientation relative to the biopsy path thereby mitigating foreshortening effects in x-ray image data; and
wherein the SPECT cameras are retracted into a stowed position during XCT imaging.

22. The method according to claim 21, further comprising rotating a gantry, to which the SPECT cameras, the x-ray source and the flat-panel x-ray detector are mounted, at a speed of 5 rpm or less.

* * * * *